United States Patent [19]

Liu

[11] Patent Number: 4,708,949

[45] Date of Patent: Nov. 24, 1987

[54] THERAPEUTIC COMPOSITION FROM PLANT EXTRACTS

[76] Inventor: Yaguang Liu, 67-08 168th St., Fresh Meadows, N.Y. 11365

[21] Appl. No.: 779,437

[22] Filed: Sep. 24, 1985

[51] Int. Cl.⁴ .................. A61K 31/705; A61K 31/70; A61K 31/495; A61K 31/34
[52] U.S. Cl. ........................................ 514/26; 514/27; 514/255; 514/468; 514/824; 514/951; 424/451; 424/464
[58] Field of Search ...................... 424/195.1, 451, 464; 514/26, 255, 27, 468, 824, 951

[56] References Cited

U.S. PATENT DOCUMENTS 3,949,074 4/1976 Eberlein et al. ...................... 514/26
4,361,152 11/1981 Ponpipom ............................ 514/26

FOREIGN PATENT DOCUMENTS 0013470 4/1978 European Pat. Off. .............. 514/27
0164720 3/1983 Japan ..................................... 514/26
0163322 3/1983 Japan ..................................... 514/26
0164721 3/1983 Japan ..................................... 514/26
0227823 6/1983 Japan ..................................... 514/26

*Primary Examiner*—Alan Siegel
*Assistant Examiner*—John W. Rollins, Jr.
*Attorney, Agent, or Firm*—Kirschstein, Kirschstein, Ottinger & Israel

[57] ABSTRACT

Therapeutic compositions are composed of four plant extracts: ginsenoside, tetramethyl pyrazine, astragalan and atractylol. Pharmaceutical dosage units are prepared by conventional means with specific weight ranges and proportions of each of the four ingredients. The pharmaceutical dosage units are highly effective in treating cerebral vascular disease and the sequelae thereof. The dosage units are also useful for bolstering immunofunction in healthy and diseased patients.

17 Claims, No Drawings

THERAPEUTIC COMPOSITION FROM PLANT EXTRACTS

BACKGROUND OF THE INVENTION

1. Field of the Invention

The present invention relates to therapeutic compositions useful for the treatment of cerebral vascular disease as well as compositions which bolster immune function and prevent infectious disease.

2. Description of the Prior Art

A plethora of pharmaceutical agents having varying degrees of effectiveness are commonly utilized for the treatment of the cerebral vascular disease. Few effective agents of any type are known in the prior art, however, for the alleviation of acute episodes of cerebral vascular insufficiency and the sequelae of such episodes, including hemiplegia, paraplegia, loss of neurofunction and so on.

Similarly, there are vitually no safe and effective drugs which enhance immune function in patients subject to serious immune compromise.

Finally, there are no pharmaceutical agents available in the prior art which exhibit low toxicity and can be administered on a long-term basis to healthy human patients to bolster immune function and reduce the incidence and severity of infectious disease. Although a number of health foods and so-called "organic" regimens of diet with vitamin and mineral supplements have been proposed in recent years to help reduce the incidence of systemic infection in healthy individuals, none of these programs have been shown consistently effective, and some have proven unsafe over the long term.

SUMMARY OF THE INVENTION

Objects of the Invention

It is an object of the present invention to provide orally ingestible and parenterally administrable compositions of very low toxicity which are effective in treating all stages of cerebral vascular disease and the sequelae of such disease.

An additional object of the present invention is to provide compositions as described above which enhance immune function to prevent the onset of infectious disease.

Another object of the present invention is to provide compositions as described above which comprise only naturally occurring plant extracts as active ingredients.

Yet a further object of the present invention is to provide compositions as described above which do not suffer from the drawbacks of pharmaceutical agents currently utilized to treat the conditions indicated.

Still a further object of the present invention is to provide methods of treating patients with the compositions described above in dosage forms including tablets, capsules, elixirs and injectable solutions.

Yet another object of the present invention is to provide compositions as described above which in low concentrations may be ingested on a regular basis as a health food.

Yet an additional object of the present invention is to provide methods of preparing compositions as described above.

Brief Description of the Invention

In keeping with these objects and other objects which will become apparent hereinafter, the present invention resides, briefly stated, in compositions comprising a mixture of the following four plant extracts.:

1. Ginsenoside extracted from ginseng (e.g., indigenous American ginseng, *Panax quinquefolium L.*, or Panax ginseng C.A. Mey.
2. Tetramethyl pyrazine extracted from the root of *Ligusticum chuanxion* Hort, or chemically synthesized.
3. Astragalan extracted from *Astragalus membranaceous* or other species of *Astragalus*.
4. Atractylol extracted from *Atractylodes macrocephala* Koidz.

For the sake of convenience, compositions comprising mixtures of the above extracts will hereinafter be referred to as "GPAA".

Although all of the above plant extracts have been individually utilized in traditional Chinese herbal medicine for a variety of treatments, no medicinal composition comprising solely these four specific principles has been prepared, and it has not been previously disclosed that the four components in combination would produce a compostion with the remarkable synergistic therapeutic effects of the compositions of the present invention.

The active principles which constitute the ingredients of GPAA can be extracted from their respective plant sources by conventional means and are purified by precipitation or recrystallization from appropriate solvents, as will be set forth in greater detail.

GPAA can be administered to patients in the form of capsules containing a powdered mixture of the active ingredients in appropriate proportions. Alternatively, tablets can be prepared comprising the active ingredients and pharmaceutically acceptable binders, excipients, lubricants, sweeteners and coatings. A syrup or elixir may be prepared by dissolving GPAA in alcohol and water together with suitable preservatives, sweeteners, dyes and flavoring agents. Ampules or vials for injection may likewise be prepared, with the GPAA as prepared for oral administration being purified through further recrystallization and sterilization and the addition thereto of distilled water and other suitable solvents and additives known in the pharmaceutical art.

The GPAA dosage units prepared according to the invention can be administrered to patients with a very low incidence of side effects and very low toxicity, and are remarkably effective in treating cerebral vascular disease and the sequelae thereof, and in enhancing immune function in healthy and diseased patients.

DETAILED DESCRIPTION OF THE INVENTION

The compositions of the present invention all include as their active component GPAA, which, as indicated previously, consists of a mixture of four plant extracts: ginsenoside, tetramethyl pyrazine, astragalan and atractylol.

The ginsenoside is extracted from dried ginseng powder, for example powdered root of *Panax quinquefolium L.* or Panax ginseng C.A. Mey. It consists of a mixture of panaxatriol and related substances, all containing a steriod nucleus and having the following general structural formula:

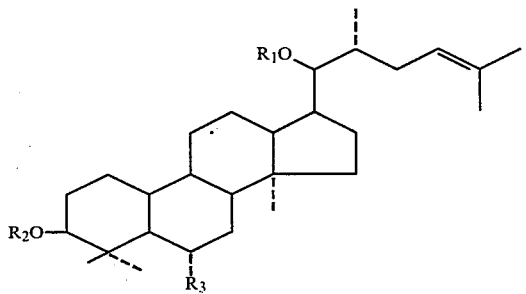

wherein, $R_1$ is 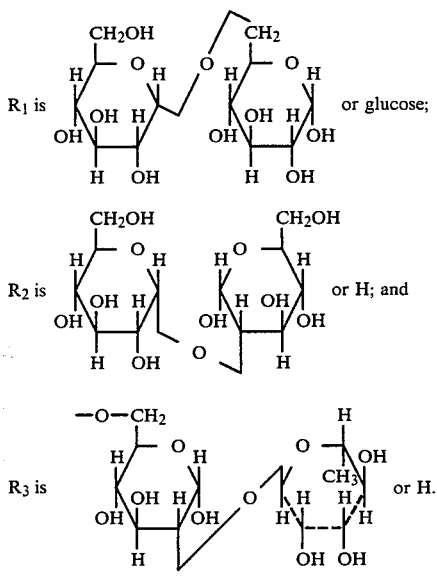 or glucose;

$R_2$ is ... or H; and $R_3$ is 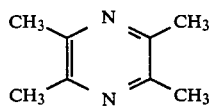 or H.

The ginsenoside extract has a melting point generally in the range of 192° to 202° C.

Extraction of ginsenoside can be carried out by any conventional means known in the art for the extraction of chemically simialr principles from plant sources. A preferred method of extraction entails the addition of ethanol to the dried ginseng powder, filtering, and repeatedly extracting the residue with ethanol. The residue is then extracted with ether, butanol and acetone, washed with acetone and ether and dried, yielding a white or ilght yellow powder which is the desired ginsenoside product.

Tetramethyl pyrazine has the following structural formula:

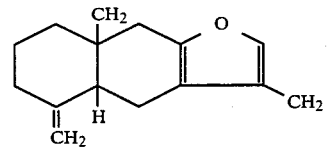

It can be obtained either by conventional methods of extraction from Ligusticum or by chemical synthesis.

A preferred method of extraction of tetramethyl pyrazine for the purposes of preparing GPAA involves the addition of ethanol to powdered root and stem of *Ligusticum chuanxiong* Hort. After refluxing and repeated extractions, the residue is dissolved in warm water, cooled and extracted with petroleum ether. The ether phase is extracted with acid, and the water phase made alkaline, and extracted with chloroform and petroleum ether, with the residue dissolved in warm water and distilled. When the distillate cools, tetramethyl pyrazine crystals form which are recovered and recrystallized. The resulting product has a melting point of about 87.5–88.8° C.

The astragalan component of the GPAA compositions of the present invention is preferably extracted from the dry powder of *Astragalus membranaceous* by an initial water extraction, then repeated extractions with ethanol, acetone and ether. After drying, the resulting product is astragalan powder. Astragalan can be derived from the roots of other species of the genus Astragalus as well for purposes of the present invention. Astragalan has the following structural formula:

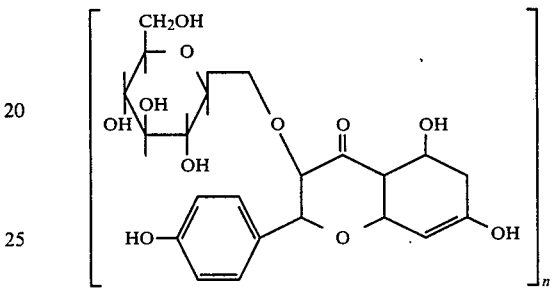

The actractylol component of GPAA is preferably prepared by extraction with ether from powdered *Atractylodes macrocephala* Koidz, although other members of the genus Atractylodes can be utilized. After refluxing and repeated filtration, atractylol is obtained by fractional distillation under reduced pressure. Atractylol has the following structural formula:

To prepare GPAA the four plant extracts prepared as indicated above are thoroughly mixed to form a dry, homogeneous composition. To achieve the therapeutic activities described herein, the preferred proportions by weight of the individual components in the GPAA are 5 to 15% ginsenoside, 30 to 50% tetramethyl pyrazine, 30 to 50% astragalan and 5 to 15% atractylol.

Pharmaceutical dosage units suitable for administration to patients may be easily prepared utilizing the dry GPAA mixture. By way of example, the mixture can be inserted into standard gelatin capsules or other suitable encapsulation materials known in the pharmaceutical art which dissolve in the digestive tract of a patient, so that the GPAA can be absorbed into the patient's bloodstream.

It has been found that appropriate, medically effective dosage forms can be prepared by enclosing in suitable capsules a GPAA mixture including about 5 to 15 mg. of ginsenoside, 25 to 300 mg. of tetramethyl pyrazine, 25 to 300 mg. of astragalan and 5 to 50 mg. of atractylol. The preferred proportions for the components in a GPAA dosage unit capsule are 25 mg. of ginsenoside, 100 mg. of tetramethyl pyrazine, 100 mg. of astragalan and 25 mg. of atractylol.

As noted above, GPAA prepared according to the present invention preferably consists of about 5 to 15% ginsenoside, about 30 to 50% tetramethyl pyrazine, about 30 to 50% astragalan and about 5 to 15% atractylol, and the weight proportions indicated above for the GPAA components in capsule form conform to these weight percentages.

Tablets can be prepared by mixing the GPAA with suitable binders, excipients, disintegration agents, lubricants and sweeteners. Examples of widely used, pharmaceutically acceptable tablet ingredients are corn starch or gelatin as binders, dicalcium phosphate as an excipient, corn starch, potato starch or alginic acid as disintegration agents, magnesium stearate as a lubricant, and sucrose or lactose as sweetening agents. The tablets may be coated with shellac or sugar to facilitate swallowing. The preferred weight ranges of the components in the GPAA tablets are the same as given above for capsule dosage forms. The most preferred weight values for the components are, as in the case of capsules, 25 mg. of ginsenoside, 100 mg. of tetramethyl pyrazine, 100 mg. of astragalan, and 25 mg. of atractylol per dosage unit.

Elixirs or syrups may be prepared by dissolving GPAA in a mixture of water and alcohol and, if desired, adding a sweetener such as sucrose, a suitable preservative, a dye (chosen according to the desired coloration) and a flavoring agent, such as an orange or cherry flavor. The concentration ranges of the GPAA components per teaspoon (5 milliliters) of syrup are the same as given above for capsule and tablet dosage units. The most preferred concentrations are 25 mg. of ginsenoside, 100 mg. of tetramethyl pyrazine, 100 mg. of astragalan, and 25 mg. of atractylol per 5 milliliters.

Ampules or vials for injection may be prepared by further refining the GPAA through water and alcohol extractions and dissolving the purified product in distilled water. Supplementary agents such as isopropyl alcohol and pharmaceutical glycerine may be added for intramuscular injections. Two milliliter vials or ampules can be prepared as describe above with each milliliter containing a pharmaceutically effective amount of GPAA. It has been found that the most effective concentration ranges for GPAA components per milliliter of injectable solution are 0.5 to 5 mg. of ginsenoside, 5 to 50 mg. of tetramethyl pyrazine, 5 to 50 mg. of astragalan, and 0.5 to 5 mg. of atractylol. The preferred concentrations are 2 mg. of ginsenoside, 20 mg. of tetramethyl pyrazine, 20 mg. of astragalan, and 2 mg. of atractylol per milliliter.

A health food suitable for daily consumption by even healthy individuals may be prepared according to the present invention with GPAA mixed with suitable food bases, flavorings, additives and preservatives. The recommended dosage range of GPAA per serving is about 20% of that of the oral pharmaceutical dosage units; i.e., each serving should contain acout 1 to 10 mg of ginsenoside, 5 to 60 mg. of tetramethyl pyrazine, 5 to 60 mg. of astragalan and 1 to 10 mg. of atractylol.

GPAA administered in pharamceutical dosage units as described above exhibits remarkable medicinal properties while having very low toxicity and a very low incidence of adverse side effects. GPAA is exceptionally effective in the treatment of patients who have suffered from episodes of cerebrovascular insufficiency, such as stroke. Administration of effective amounts of GPAA, such as 3-4 of the capsules or tablets described above administered daily, alleviates the sequelae such as hemiplegia, paraplegia and impaired neurofunction, and greatly shortens the required periods of convalescence and rehabilitation.

Furthermore, GPAA is useful in treating patients with a history of acute occlusive cerebral vascular episodes and in preventing or mitigating further episodes of the same type.

It is believed that the effectiveness of GPAA in treating cerebral vascular disease results from its ability to promote dissolution of atherosclerotic plaque and prevent further local plaque formation. In addition, GPAA acts on nerve endings through neuro-mediators to relax vascular spasm. The resultant decrease in occlusion and spasm of the cerebral circulatory system enagles symptomatic and long-term relief.

As noted above, the toxicity and incidence of side effects associated with the administration of GPAA, whether by oral or parentheral routes, is extremely low in comparison with agents presently used to treat vascular disease. The intravenous $LD_{50}$ of GPAA in mice is 956 mg./kg..

Another remarkable feature of the GPAA compositions of the present invention is their level of activity in bolstering immune function and decreasing the susceptibility of patients to infectious disease. The ability of GPAA to enhance both humoro- and cell-mediated immunity has been demonstrated pharmacologically, as will be set forth below.

GPAA is also of value in reducing the risk of pathogenic infection in other types of patients experiencing immune system compromise, such as victims of severe burns, and asthmatics and others undergoing intensive corticosteriod therapy.

Because of its low toxicity and its unique ability to bolster immune function, GPAA can also be administered orally to other classes of patients in connection with whom it is particularly desirable to avoid the onset of infectious disease, such as elderly patients, patients with weakened hearts or patients who have difficulty breathing, and may even be utilized by healthy patients to help ward off common systemic infectious. GPAA may be consumed daily as a health food, with the dosage range about 20% of that of the oral dosage forms or about 1 to 10 mg. of ginsenoside, 5 to 60 mg. of tetramethyl pyrazine, 5 to 60 mg. of astragalan and 1 to 10 mg. of atractylol per serving.

The following specific examples will provide detailed illustrations of methods of producing GPAA according to the present invention and pharmaceutical dosage units containing GPAA. Moreover, examples will be given of pharmaceutical testing performed with GPAA which demonstrates its effectiveness in bolstering immunofunction. These examples are not intended, however, to limit or restrict the scope of the invention in any way, and should not be construed as providing conditions, parameters, reagents, or starting materials which must be utilized exclusively in order to practice the present invention.

EXAMPLE 1

Extraction of Ginsenoside 2,000 ml of 95% ethanol was added to 1,000 g of dried powder of ginseng derived from *Panax quinquefolium* and allowed to stand for one day at room temperature. The solution was filtered and the extract filtrate saved. 2,000 ml of ethanol was added to the residue and refluxed in a water bath for 6 hours. The refluxing was repeated twice by collecting the alcohol, replacing it with an equal volume of fresh 95% ethanol and refluxing for 6 hours. The refluxed alcohol was cooled and filtered and the filtrate combined with the extract filtrate. Ethanol was then recovered by reduced pressure distillation and the residue dissolved in 500 ml of distilled water. The lipid component was removed with 5 changes of ether by adding 500 ml to the water phase for each extraction. An equal volume of water-saturated butanol was added to the final water phase and the butanol was then distilled under reduced pressure. The residue powder was dissolved in 500 ml of ethanol and 2,000 ml of acetone was added to the alcohol with constant stirring while a precipitate formed. The precipitate was washed twice each with acetone and ether and dried. The resulting white or light yellow powder was the final product, i.e., ginsenoside.

EXAMPLE 2

Extraction of Tetramethyl Pyrazine 2,000 ml of ethanol was added to 1,000 g of powdered root and stem of *Ligusticum chuanxion* Hort and refluxed in a water bath for 2 hours. The extraction was repeated twice with fresh alcohol and further refluxing. The alcohol was recovered by concentration under reduced pressure. The residue was dissolved in warm water, cooled to room temperature and extracted twice with equal volumes of petroleum ether. The ether phase was then extracted with an equal volume of I N HCl. Sodium carbonate was added to the water phase until its pH was 9–10, and the water phase was then extracted with an equal volume of chloroform. The chloroform phase was collected and chloroform recovered under reduced pressure. The residue gel was dissolved in petroleum ether. The ether was evaporated under reduced pressure and the residue dissolved in a mixture of petroleum ether and chloroform (8:2). The solvent was then evaporated under reduced pressure and the solid residue dissolved in warm water. The solution was cooled to room temperature and the pH adjusted to 8–9 with saturated NaOH. After distillation, collection of the distillate and cooling, needle crystals formed which were then dissolved in warm water and filtered. The product was recrystallized once by repeating the above procedure. The final tetramethyl pyrazine product was dried under vacuum and was found to have a melting point of 87.5°–88.8° C.

EXAMPLE 3

Extraction of Astragalan 2,000 ml of water was added to 1,000 g of dry powder of *Astragalus membranaceous*. The solution was heated to boil and simmered for one and one-half hours after boiling. This water extraction was repeated once and the two extracts combined and filtered. The filtrate was concentrated under reduced pressure to approximately 500 ml and 95% ethanol was added to the concentrate to a final alcohol concentration of 60%. The solution was filtered and the precipitate dissolved in an appropriate amount of water, spun to remove the residue and filtered. The filtrate was concentrated under reduced pressure to 100 ml and 95% ethanol added to the concentrate to a final alcohol concentration of 80%. The solution was allowed to stand at 4° C. overnight. The supernatant was then dissolved and the precipitate washed three times with 95% ethanol and then twice with acetone and ether consecutively. The product was vacuum dried, and the resulting powder was astragalan.

EXAMPLE 4

Extraction of Atractylol 1,000 ml of ether was added to 100 g of *Atractylodes macrocephala* Koidz powder and refluxed in a water bath for 3 hours. This procedure was repeated twice with fresh ether. The ether layers were then combined and filtered, allowed to stand 24 hours and filtered again. The filtrate was passed through aluminum oxide to obtain clear liquid. After fractional distillation at a pressure of 4 mm Hg, atractylol was obtained by collecting the distillate at 100°–130° C.

EXAMPLE 5

Preparation of GPAA

5 Kg of ginsenoside, 20 Kg of tetramethyl pyrazine, 20 Kg of astragalan, and 5 Kg of atractylol, all produced in accordance with the preceding examples, were thoroughly mixed and agitated until a homogeneous mixture of the four components was obtained.

EXAMPLE 6

GPAA Tablets

5 Kg of GPAA produced in accordance with the preceding example was combined with corn starch, dicalcium phosphate, potato starch, magnesium stearate and lactose. After further mixing, the aggregate was inserted into a tablet press and compressed into tablets suitable for oral administration. Each tablet contained 25 mg of ginsenoside, 100 mg of tetramethyl pyrazine, 100 mg of astragalan and 25 mg of atractylol.

EXAMPLE 7

GPAA Injectable Solution

1 Kg of ginsenoside, 10 Kg of tetramethyl pyrazine, 10 Kg of astragalan, and 1 Kg of atractylol were thoroughly mixed in accordance with Example 5. The resulting GPAA powder was dissolved in a sufficient amount of sterile water and 4 volumes of 95% ethanol were added. The solution was allowed to stand for 24 hours and then filtered, with the ethanol being recovered under reduced pressure. 6 volumes of 95% ethanol were added to the residue. After standing for another 24 hours, the solution was filtered and ethanol recovered under reduced pressure. The residue was then distilled until there was no remaining smell of alcohol. Sufficient distilled water was added to dissolve the residue, and the solution was filtered to remove any undissolved material. Pharmaceutical glycerine was added to the solution. The solution was then fine filtered, and the volume adjusted to 500 liters with distilled water. After additional fine filtering, the solution was sealed in 2 ml sterile ampules which were further sterilized and sealed. Each ampule contained 2 mg of ginsenoside, 20 mg of tetramethyl pyrazine, 20 mg of astragalan and 2 mg of atractylol per milliliter of solution.

The following examples relate to in vitro pharmacological testing that was performed with GPAA administered to an experimental group of laboratory animals and certain factors of significance in determining the level of immunoactivity compared to a control group. As will be shown, in each instance the experimental group to which GPAA had been administered showed a greater level of immunoactivity than the control group.

EXAMPLE 8

Hemolytic Plaque Test

1. Materials:
   a. Sheep red blood cells (SRBC)
   b. Complement — Pooled guinea pig sera, used at 1:5 dilution
   c. Mice — 20–25 g
2. Methods:
   Each mouse was injected with 0.2 ml of 10% SRBC intraperitoneally daily for 4 days. Experimental animals received 0.2 ml of GPAA at the same time through the same route while 0.2 ml of normal saline was administered to the control group instead. The animals were sacrificed on the 5th day, the spleens removed and homogenized. Spleen cells were collected and suspended to a concentration of $10^7$/ml. 0.1 ml of 10% SRBC ($2 \times 10^8$) was added to 0.1 ml spleen cell suspension ($1 \times 10^6$), suspended in 0.7% agarose and poured into petri dishes. After incubation at 37° C. for 1 hour, 1 ml of complement was added to each dish. The incubation was continued for another 2 hours, and the number of hemolytic plaques per $1 \times 10^6$ spleen cells per dish determined.
3. Result:

|  | Number of Subjects | Mean # hemolytic plaques/$1 \times 10^6$ cells* |
|---|---|---|
| Control | 12 | 28.48 |
| Experimental | 14 | 39.52 |

$P < 0.01$
*Measure of B-cell activity.

EXAMPLE 9

Influence of GPAA on Complement

1. Materials:
   a. Veronal buffer stock:
      NaCl 85.00 g., barbituric acid 5.75 g., sodium barbital 3.75 g. Add 1500 ml of distilled water and heat to dissolve, add distilled water to 2,000 ml.
   b. 0.1 M EDTA — Na$_3$ stock:
      EDTA — Na$_3$ 37.23 g NaOH 4.00 g
      Add the EDTA — Na$_3$ to 500 ml of distilled water and the NaOH to 100 ml of distilled water. Add the latter to the former and EDTA — Na$_3$ will dissolve instantly. Adjust pH to 7.5 with 1N NaOH and add distilled water to 1000 ml.
   c. 2% gelatin:
      Gelatin 2.0 g, distilled water 100 ml. Heat to dissolve or autoclave and store at 4° C.
   d. Gelatin Veronal Buffer (GVB)

| Veronal buffer stock | 100 ml |
|---|---|
| 0.03 M CaCl$_2$ | 10 ml |
| 0.01 M MgCl$_2$ | 10 ml |
| 2% Gelatin | 100 ml |
| Add distilled water to | 1000 ml | e. Alsever Solution:
      Glucose 20.5 g, NaCl 4.2 g, sodium citrate 8.0 g. Dissolve in approximately 800 ml of distilled water and adjust pH to 6.1 with citric acid. Add distilled water to 1000 ml. Sterilize by autoclaving.
   f. 0.01 M EDTA — GVB:
      Veronal buffer stock 360 ml 0.1 M EDTA — Na$_3$ stock 200 ml, 2% gelatin 100 ml, add distilled water to 2000 ml.
   g. SRBC:
      Mix fresh sterile sheep blood with equal volume of Alsever solution and store at 4° C. It can be used for several weeks.
   h. Hemolysin:
   (1) Preparation of SRBC stroma:
      Spin down the SRBC in 1 lister of sheep blood-Alsever solution (g) and wash several times with normal saline. Add 10 liters of distilled water which contains 4 ml of glacial acetic acid. Suspend the RBC and sit in a 4° C. refrigerator overnight. Discard the supernatant and pack the settled stroma at 2,000 rpm. Suspend the supernatant and pack the settled stroma at 2,000 rpm. Suspend the stroma in a 0.01 M acetic acid, pH 5.0 and, wash 5 times with the acetic acid solution. The acetic acid is then removed and the pH brought to neutral or slightly alkaline by washing the stroma 3 times each with 0.1 M Na$_2$HPO$_4$ and normal saline. Heat to 100° C. for 1 hour. Determine the nitrogen content and adjust with sterile normal saline to 1 mg/ml. Add 0.01% merthiolate and store at 4° C.
   (2) Immunization of rabbits:
      Immunize the rabbits by 11 intravenous injections of the SRBC stroma in 2 weeks. Bleed the animals 4 days after the last injection. Separate the serum. Inactivate at 56° C. for 30 minutes and store at −20° C.
   (3) Titration for optimal concentration of hemolysin:
      By using 50% hemolysis (C'H$_{50}$) as end-point, SRBC sensitized by various concentrations of hemolysin are titrated against various amounts of guinea pig complement. Optimal concentration of hemolysin is determined by OD$_{541}$ reading which gave C'H$_{50}$, and standard curve is plotted.
   i. Serum samples for determination of complement contents: Collect blood and separate serum.
2. Methods:
   a. Preparation of SRBC suspension—wash SRBC 5 times with GVB to free from platelets. Filter through gauze to remove cell aggregates. Adjust the SRBC suspension to $1 \times 10^9$ RBC/ml.
   b. Preparation of sensitized SRBC — warm up 1 volume of hemolysin at the optimal concentration in a 37° C. water bath for 10 minutes and add an equal volume of SRBC suspension at $1 \times 10^9$ cells/ml with stirring. Sit in a water bath at 37° C. with shaking for 30 minutes. Then bring the termperature down in an ice-cool water bath with shaking. Wash the cold SRBC once with 0.01 M EDTA — GVB, twice with GVB and prepare sensitized SRBC suspension at $5 \times 10^8$ cells/ml with GVB.
   c. Determine C'H$_{50}$ unit and plot of standard curves for the serum samples.

3. Results:

| | Number of Subjects | Units (C'H$_{50}$)/ml* |
|---|---|---|
| Control | 8 | 247 ± 10 |
| GPAA Treated | 8 | 356 ± 10 |

$P < 0.05$
*Measure of complement in serum.

The plant substances from which the components of GPAA are extracted are readily and widely available in North America and Eastern Asia. For example, *Panax guinquefolium L.* grows abundantly in the Wisconsin area.

The preparation of GPAA is simple and can be accomplished by the extraction methods set forth above or any conventional methods for extracting the active principles from the plant tissues. The novelty of the present invention resides in the mixture of the active principles in the specified proportions to produce GPAA, and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, capsules, tablets, syrups, elixirs, and solutions for parenteral injection with specified ranges of GPAA concentration.

In addition, the present invention provides novel methods for treating a variety of disease conditions and bolstering immunofunction with one easily produced, safe pharmaceutical agent.

It will thus be shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims.

1. A composition comprising a mixture of:
   (a) about 5 to 15% by weight ginsenoside;
   (b) about 30 to 50% by weight tetramethyl pyrazine;
   (c) about 30 to 50% by weight astragalan; and
   (d) about 5 to 15% by weight atractylol.

2. A composition according to claim 1 wherein said ginsenoside is extracted from *Panax quinquefolium L.*, said tetramethyl pyrazine is extracted from *Lingusticum chuanxion* Hort, said astragalan is extracted from *Astragalus membranaceous* and said actractylol is extracted from *Atractylodes macrocephala* Koidz.

3. A composition according to claim 1, wherein said ginsenoside is extracted from *Panax ginseng,* C. A. Mey.

4. A pharmaceutical dosage unit for the treatment of cerebrovascular insufficiency, occlusive cerebral vascular disease, stroke and the resulting paraplegia, hemiplegia and impaired neurofunction, said dosage unit comprising a mixture of about 5 to 15% ginsenoside, about 30 to 50% atractylol by weight in a pharmaceutically acceptable dosage form.

5. A dosage unit according to claim 4 wherein said dosage form is an orally ingestible capsule.

6. A dosage unit according to claim 4 wherein said dosage form is a tablet which includes in addition pharmaceutically acceptable binders and excipients.

7. A dosage unit according to claims 5 or 6 which comprises 5 to 50 mg of ginsenoside, 25 to 300 mg of tetramethyl pyrazine, 25 to 300 mg of astragalan and 5 to 50 mg of atractylol.

8. A dosage unit according to claim 8 which comprises about 25 mg of ginsenoside, 100 mg of tetramethyl pyrazine, 100 mg of astragalan, and 25 mg of atractylol.

9. A dosage unit according to claim 4 wherein said dosage form is a syrup or elixir which includes in addition a liquid vehicle suitable for oral administration.

10. A dosage unit according to claim 4 wherein said dosage form is a solution for parenteral injection which includes in addition a liquid vehicle suitable for parenteral administration 11. An injectable solution according to claim 10 comprising about 0.5 to 5 mg of ginsenoside, 5 to 50 mg of tetramethyl pyrazine, 5 to 50 mg of astragalan and 0.5 to 5 mg of atractylol per milliliter.

12. An injectable solution according to claim 11 which comprises about 2 mg of ginsenoside, 20 mg of tetramethyl pyrazine 20 mg of astragalan and 2 mg of atractylol per milliliter.

13. A method of treating a patient suffering from cerebrovascular insufficiency, occlusive cerebal vascular disease, stroke and the resulting paraplegia, hemiplegia and impaired neurofunction, consisting of the administration to the patient of a pharmaceutical dosage unit including as its active ingredient a composition comprising about 5 to 15% ginsenoside, 30 to 50% tetramethyl pyrazine, 30 to 50% astragalan and 5 to 15% atractylol by weight.

14. A method according to claim 13 wherein said composition is orally administered to the patient in the form of a capsule 3 to 4 times daily.

15. A method according to claim 13 wherein said composition is orally administered to the patient in the form of a tablet 3 to 4 times daily.

16. A method according to claim 13 wherein said mixture is orally administered to the patient in the form of a syrup or elixir 3 to 4 times daily.

17. A method according to claim 13 wherein the mixture is parenterally administered to the patient in the form of an injectable solution.

* * * * *